(12) United States Patent
Gangaikondan-Iyer et al.

(10) Patent No.: US 11,443,835 B1
(45) Date of Patent: Sep. 13, 2022

(54) METHODS AND SYSTEMS FOR PROCESSING DATA INQUIRES

(71) Applicant: Express Scripts Strategic Development, Inc., St. Louis, MO (US)

(72) Inventors: Harry S. Gangaikondan-Iyer, St. Louis, MO (US); William S. Patterson, St. Louis, MO (US); Stephen A. Randall, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 708 days.

(21) Appl. No.: 15/640,396

(22) Filed: Jun. 30, 2017

(51) Int. Cl.
*G16H 10/00* (2018.01)
*G06Q 10/10* (2012.01)
*H04W 4/02* (2018.01)

(52) U.S. Cl.
CPC ............. *G16H 10/00* (2018.01); *G06Q 10/10* (2013.01); *H04W 4/025* (2013.01)

(58) Field of Classification Search
CPC ................................................ G06Q 50/22–24
See application file for complete search history.

(56) References Cited

U.S. PATENT DOCUMENTS

| 7,493,263 | B2 | 2/2009 | Helmus et al. |
| 7,624,207 | B2 * | 11/2009 | Marcotte ................. G06F 9/544 |
| | | | 710/52 |
| 7,734,483 | B1 | 6/2010 | Smith et al. |
| 8,099,295 | B2 | 1/2012 | Virdee et al. |
| 8,335,695 | B2 | 12/2012 | Cedergreen |
| 10,599,612 | B1 * | 3/2020 | Gralnick ................ G06F 16/252 |
| 2002/0103680 | A1 * | 8/2002 | Newman ................ G06Q 30/02 |
| | | | 705/4 |

(Continued)

FOREIGN PATENT DOCUMENTS

CA 2531875 A1 * 7/2006 ............. G06Q 10/10

OTHER PUBLICATIONS

Abdullah et al., "Comparative Study of Medical Claim Scrubber and a Rule Based System," This work has been supported by Higher Education Commission of Pakistan under '5000—indigenous PhD Fellowships Scheme' (Year: 2009).*

*Primary Examiner* — Jason B Dunham
*Assistant Examiner* — Jonathon A. Szumny
(74) *Attorney, Agent, or Firm* — Husch Blackwell LLP

(57) ABSTRACT

Methods and systems for processing data inquiries are described. In one embodiment, data from a data source can be received, a data processing request indicating a request to perform a first function can be received, and a first identifier associated with a user can be determined based on the received data. A table storing a plurality of adjudication results including a plurality of field parameters may be accessed. The plurality of adjudication results in the table can be filtered by determining which of the plurality of adjudication results includes one of the plurality of field parameters having a value that matches or corresponds to the selected field value to create a first subset of filtered adjudication results from the plurality of adjudication results. The first subset of adjudication results can be transmitted when the processor determines that at least one adjudication result of the plurality of adjudication results is within the first subset. Additional methods and systems are disclosed.

17 Claims, 6 Drawing Sheets

(56) References Cited

U.S. PATENT DOCUMENTS

| | | | |
|---|---|---|---|
| 2005/0137912 A1* | 6/2005 | Rao | G06Q 10/10 |
| | | | 705/4 |
| 2009/0287509 A1* | 11/2009 | Basak | G06Q 10/10 |
| | | | 705/4 |
| 2010/0293000 A1* | 11/2010 | Hu | G06Q 10/087 |
| | | | 705/2 |
| 2014/0337442 A1* | 11/2014 | Zhuang | H04L 51/066 |
| | | | 709/206 |
| 2015/0242584 A1* | 8/2015 | Butler | G06Q 10/10 |
| | | | 705/2 |
| 2018/0225773 A1* | 8/2018 | Kinney | G06Q 40/08 |

* cited by examiner

METHODS AND SYSTEMS FOR PROCESSING DATA INQUIRES

FIELD

The present disclosure relates generally to the technical field of processing data inquires. In a specific example, the present disclosure may relate to the processing data inquires by referencing to a look-aside table.

BACKGROUND

Servers that receive and respond to data inquires can quickly become overloaded when the number of data inquires increases significantly. For example, computing resource capacity is significantly strained due to numerous data inquires. Servers are even more burdened by limited bandwidth when the process of responding to data inquires requires significant processing using numerous variables. As an example server burdened by limited bandwidth, pharmacy benefit managers (PBMs) may perform claim adjudication as part of an offered benefit plan design that includes a prescription drug benefit. Third parties and members may submit a significant number of data inquires, and many of those data inquires may be similar in nature. Claim adjudication, in the context of a prescription drug benefit, refers to the determination of the payment or financial responsibility of a claim for the prescription drug after the prescription drug benefit of the member is applied to the prescription drug claim.

DETAILED DESCRIPTION

Figure 1:
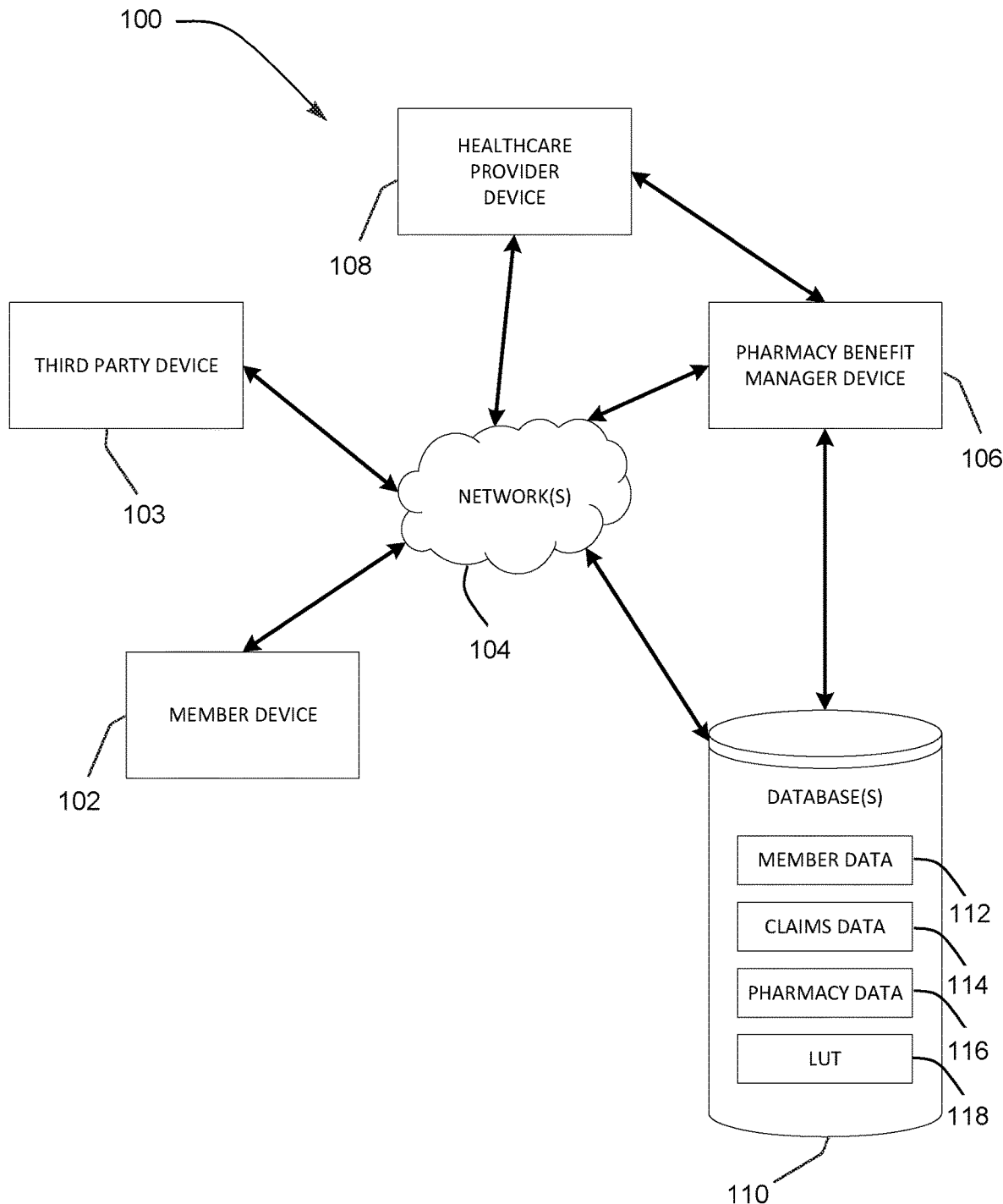
FIG. 1 is a block diagram of an example system, according to an example embodiment.

Example methods and systems for data processing are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

Generally, a client engages a PBM to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then may adjudicate the claim associated with the prescription drug and provides a response to the pharmacy following performance of the aforementioned functions. As part of the adjudication, the client (or the PBM on behalf of the client) may ultimately reimburse the pharmacy for filling the prescription drug when the prescription drug was successfully adjudicated. The aforementioned adjudication functions generally occur before the co-pay is received and the prescription drug is dispensed. However, the operations may occur simultaneously, substantially simultaneously, or in a different order. In addition, more or less adjudication functions may be performed as part of the adjudication process. In some embodiments, the PBM can perform the adjudication functions without dispensing a drug when the PBM receives a price inquiry.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

More generally, clients and third parties may query the PBM for pricing information regarding pharmaceutical drugs by submitting a price inquiry. As stated above, adjudication results in, among other things, a drug price, a co-pay price to be paid by the client, and potentially other fees passed on to the client. Clients may wish to know the drug price and co-pay amount prior to agreeing to purchase the drug and requesting that a pharmacy dispense the drug. Determining a drug price and co-pay amount may include a complete performance of the adjudication function. To provide pricing information without actually dispensing a drug, the PBM may include a dispense parameter that is part of an application programming interface ("API"), where the dispense parameter allows or prevents drug dispensing (i.e. every step of the adjudication function performed except dispensing the drug) based on the dispense parameter's value. For example, the dispense parameter may provide an indication to a pharmacy of entity filling the prescription to actually fill the prescription and provide the prescription drug to a client. A dispense value for dispense parameter may be necessary for a drug filling process to begin such that a client will actually be provided the prescription drug. If the dispense parameter does not indicate that drugs should be provided, then the process of filling a prescription and providing prescription drugs will not begin. A client or a third party may select this parameter and request price information, and the PBM may perform the adjudication function to fulfill the price inquiry. Third parties, or so-called "transparency vendors," may frequently submit price inquires as part of a service that compares drug prices among various drug benefit plan competitors. In view of all these factors, the PBM performs adjudication frequently to meet both requests from pharmacies to dispense drugs and requests by clients or third parties for drug prices and co-pay amounts. Given the numerous factors and steps of the adjudication function, frequent adjudication causes a significant burden on the PBM's computer resources. For example, third parties and clients seeking to learn prescription drug amounts may overload a system's ability to provide quotes, may cause delays in how quickly the system can provide drug price quotes, may cause delays in filling real prescription requests, may substantially burden the bandwidth of computer hardware, or may require extremely expensive computer hardware to handle these requests.

In view of these problems, the PBM may store adjudication results from the adjudication function in a look-aside table or a data computation table. The look-aside table stores adjudication results and the variables generated in the adjudication result so that requests having identical or similar variables or field parameters need not be recalculated. For example, if a first client requests a price inquiry based on a first set of variables at time A, the PBM may perform the adjudication function on the price inquiry using the first set of variables, and the PBM stores the adjudication results in the look-aside table. At time B, which is a time subsequent to time A, if the first or a second client requests a price inquiry also using the first set of variables, the PBM does not perform the adjudication function, but instead references the results in the look-aside table and provides the stored results to the second client without performing any adjudication processing. By skipping the adjudication function to fulfill the second price inquiry, the PBM saves significant processing time and resources, which can be used instead to fulfill other adjudication requests based on different variables than the first set of variables. The process described above assumes that time A and B are both made within a predetermined time period (e.g. within 24-48 hours), but the embodiments are not limited to such period. In view of using the look-aside table, the time to process a price inquiry is substantially quicker such that multiple price quotes can be provided in the time it took to perform one price quotation that involved full adjudication, the bandwidth of the system is substantially improved for responding to price inquiries, and computer hardware improvements are not required. Furthermore, computing resources necessary for filling prescriptions can be dedicated to those services.

FIG. 1 is a block diagram of an example system 100, according to an example embodiment. The system 100 includes a member device 102 in communication with a pharmacy benefit manager device 106 over a network 104. The pharmacy benefit manager device 106 may be in communication with a healthcare provider device 108 over a network 104.

The member device 102 may be used by a device operator. The device operator may be a member that is either a participant in a drug benefit plan or a beneficiary of the participant (e.g., a spouse or a child of the beneficiary). However, the device operator may be another person operating the member device 102 on behalf of the member. Examples of such other people include parents, guardians and caregivers.

The member device 102 is used by a device operator. The member device 102 may be a stand-alone device that solely provides at least some of the functionality to enable the claim adjudication for prescription drugs, or may be a multi-use device that has functionality outside of claim adjudication as described herein. Examples of the member device 102 include a set-top box (STB), a receiver card, a mobile telephone, a personal digital assistant (PDA), a display device, a portable gaming unit, and a computing system; however, other devices may also be used. For example, the member device 102 may include a mobile electronic device, such an IPHONE or IPAD device by Apple, Inc., mobile electronic devices powered by ANDROID by Google, Inc., and a BLACKBERRY device by Research In Motion Limited. The member device 102 also include other computing devices, such as desktop computing devices, notebook computing devices, netbook computing devices, gaming devices, and the like. Other types of electronic devices may also be used.

The network 104 by which the member device 102 communicates with the pharmacy benefits manager device 106 and the healthcare provider device 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a Wi-Fi network, or an IEEE 802.11 standards network, as well as various combinations thereof. Network 104 may also include optical communications. Network 104 may also include wired communication. Other conventional and/or later developed wired and wireless networks may also be used.

The system 100 may also include a third party device 103 in communication with the pharmacy benefit manager device 106 over the network 104. The third party device 103 may be used by a third party, such as a "transparency vendor" to submit price inquiries, but, in some embodiments, the third party device 103 may not request the PBM to dispense a drug. The third party device 103 may include a computing system or a server system. Other types of electronic devices may also be used.

The pharmacy benefit manager device 106 may be a device operated by an entity at least partially responsible for creation and/or management of the drug benefit plan. While the pharmacy benefit manager operating the pharmacy benefit manager device 106 is typically a PBM, or associated with a PBM, other entities may operate the pharmacy benefit manager device 106 on behalf of themselves, the PBM, or another entity.

In an example embodiment, some of the operations of the PBM that operates the pharmacy benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. The pharmacy may then submit a claim to the PBM. The PBM may perform certain claim adjudication functions including verifying the eligibility of the member, reviewing the formulary to determine appropriate co-pay, coinsurance, and deductible for the prescription drug, and performing a drug utilization review (DUR) on the member prior to receiving the prescription for the member. If the PBM receives the prescription, the PBM may adjudicate the claim associated with the prescription drug and provide a response to the pharmacy following performance of adjudication functions for the received prescription. As part of the adjudication, the client (or the PBM on behalf of the client) may ultimately reimburse the pharmacy for filling the prescription drug when the prescription drug was successfully adjudicated. As stated above, pharmacy benefit manager device 106 may perform the claim adjudication functions to respond to price inquiries from the member device 102 or the third party device 103 without requesting a pharmacy to dispense the drug. Responding to a price inquiry does not require pharmacy reimbursement or dispensing of the pharmaceutical drug.

In some embodiments, an application may be downloaded, installed, and launched on the member device 102 to enable the device operator to facilitate claim adjudication. An application may also be downloaded, installed, and launched on the third party device 103 to enable the third party to submit price inquires. The application may take advantage of hardware and/or software functionality provided by manufacturers of the member device 102/third party device 103 and/or developers of the operating system of the member device 102/third party device 103. For example, the application may use the SAFARI web browser on the IPHONE device, the Webkit browser on an ANDROID device, MOBILE INTERNET EXPLORER on a WINDOWS MOBILE device, or on any of the aforementioned devices. The application may include instructions that when executed on the member device 102 or the third party device 103, in the pharmacy benefit manager device 106, or healthcare provider device 108, cause a machine to change its state or perform tasks within the machine and with other machines. In some embodiments, the application made available for download to the third party device 103 may not be identical to the application made available for download to the member device 102 because the application executed by the third party device 103 may not request dispensing of a drug.

The application may be downloaded to a healthcare provider device 108, the pharmacy benefit manager device 106, the third party device 103, or member device 102. In some embodiments, the pharmacy benefit manager device 106 and/or the healthcare provider device 108 may be operated by an entity that makes available applications created by the application provider and/or third parties (e.g., the pharmacy benefit manager) for download and use on electronic devices. Examples of companies that operate the application provided by the pharmacy benefit manager device 106 may include Apple, Inc. through its operation of ITUNES STORE, Google, Inc. through its operation of ANDROID MARKET, AT&T through its operation of its APPCENTER, and Research In Motion Limited through its operation of BLACKBERRY APP WORLD. Each of these device companies can host and supply proprietary apps, open apps, and apps by third parties. In some embodiments, the application may be downloaded from application download sites, the PBM, healthcare provider system, and/or a web-based application distribution system that may be accessed, e.g., via a web browser executed on an electronic device, such as the member device 102 or the third party device 103.

The member device 102 may be in a client-server relationship with the pharmacy benefit manager device 106 and/or the healthcare provider device 108, a peer-to-peer relationship with the pharmacy benefit manager device 106 and/or the healthcare provider device 108, or in a different type of relationship with the pharmacy benefit manager device 106 and/or the healthcare provider device 108. The third party device 103 may be in a client-server relationship with the pharmacy benefit manager device 106 and/or the healthcare provider device 108, a peer-to-peer relationship with the pharmacy benefit manager device 106 and/or the healthcare provider device 108, or in a different type of relationship with the pharmacy benefit manager device 106 and/or the healthcare provider device 108.

The pharmacy benefit manager device 106 may be in communication directly (e.g., through local storage) and/or through the network 104 (e.g., in a cloud configuration or software as a service) with a database 110. The database 110 may store member data 112, claims data 114, pharmacy data 116, and/or a look-aside table 118. The database 110 may comprise an SQL database or a Big Data platform, such as Mongo-DB or NewSQL.

The member data 112 includes information regarding the members associated with the pharmacy benefit manager. Examples of the member data 112 include name, address, telephone number, e-mail address, prescription drug history, and the like. The member data 112 may include a client identifier that identifies the client associated with the member and/or a member identifier that identifies the member to the client (e.g. a business or insurer providing the prescription drug benefit plan). The member data 112 may include a universal identifier to identify claims associated with the member from one or more benefit plans. In some embodiments, the member data 112 may also include data regarding the benefit plan associated with the member and/or the client. The member data 112 may include an indication of authorization of whether a member has or is otherwise associated with a member device (e.g., the member device 102).

The claims data 114 includes information regarding the claims submitted by a pharmacy or the member to the pharmacy benefit manager. Examples of the claims data 114 may include data indicating eligibility for a prescription drug, access to the prescription drug, access to supporting information associated with the prescription drug, data associated with a provider of the prescription drug, demographic information associated with the member, data associated with a pharmacy dispensing the prescription drug, or any combination thereof.

The claims data 114 may be associated with a single benefit manager or multiple benefit managers. In some embodiments, the claims data 114 includes claims data for a member from a prior pharmacy benefit manager that is not the member's current pharmacy benefit manager.

The pharmacy data 116 may include information regarding pharmacies. The pharmacy data 116 may include, by way of example, location data regarding the location of the pharmacies, information data regarding the pharmacy hours and/or telephone number, pharmacy network association data defining the pharmacy network associations of which the pharmacies are associated, prescription drug availability, and the like.

The look-aside table 118 may store the adjudication results. The look-aside table 118 may store the variables or field parameters (e.g. parameters of member data 112, parameters of claims data 114, parameters of pharmacy data 116) that generated the adjudication results. The parameters used to calculate adjudication results include drug name, drug classification, pharmacy, plan design (e.g. group), price, and demographics of requester. The look-aside table 118 may also store timestamps for each adjudication result, where a time stamp is a recordation of time associated with when adjudication occurred. Furthermore, the look-aside table 118 may store a geographic indicator (e.g. GPS coordinates, a zip code, or the like) that generated the adjudication results.

In some embodiments, the look-aside table 118 may store adjudication results from pharmacy claims and from price inquiries or only from price inquiries. In some embodiments, old data (e.g. older than 48 hours old) may be purged from the look-aside table 118 or the look-aside table 118 may store adjudication results indefinitely. In some embodiments, the look-aside table 118 comprises an active table and a historical table, where the active table may store new data that has been adjudicated within a time period (e.g. within the last 24-48 hours), and the historical table may store old data that was adjudicated outside the time period (e.g. not within the last 24-48 hours). Data can be automatically moved from the active table to the historical table when the data in the active table when the time stamp of the adjudicated results reaches a time threshold (e.g. 24-48 hours).

While the system 100 in FIG. 1 is shown to include single devices 102, 103, 106, 108, multiple devices may be used. The devices 102, 103, 106, 108 may be the same type of device or may be different device types. When multiple devices are present, the multiple devices may be of the same device type or may be a different device type. Moreover, system 100 shows a single network 104; however, multiple networks can be used. The multiple networks may communicate in series with each other to link the devices 102, 103, 106, 108 or in parallel to link the devices 102, 103, 106, 108. In some embodiments, at least some of the functionality of the healthcare provider device 108 may be included in the pharmacy benefit manager device 106.

Figure 2:
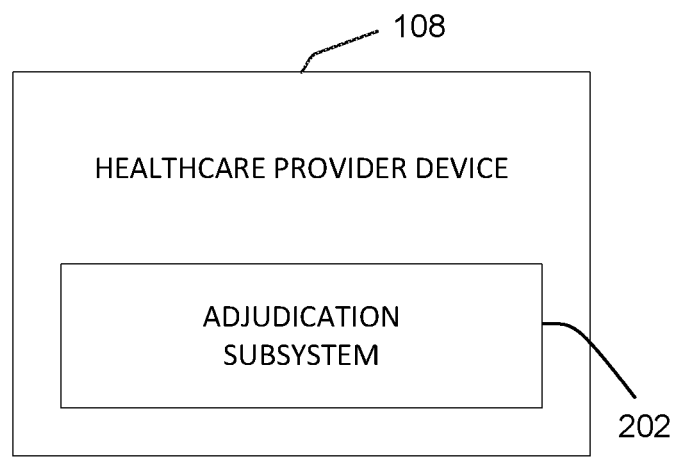
FIG. 2 is a block diagram of an example healthcare provider device that may be deployed within the system of FIG. 1, according to an example embodiment.

FIG. 2 illustrates the healthcare provider device 108, according to an example embodiment. The healthcare provider device 108 may be used by a healthcare provider operator prescribe a prescription drug for the member. The healthcare provider device 108 may be deployed in the system 100, or may otherwise be used.

The healthcare provider device 108 may include an adjudication subsystem 202. The adjudication subsystem 202 enables the device operator of the healthcare provider device 108 to adjudicate claims associated with prescription drugs.

Figure 3:
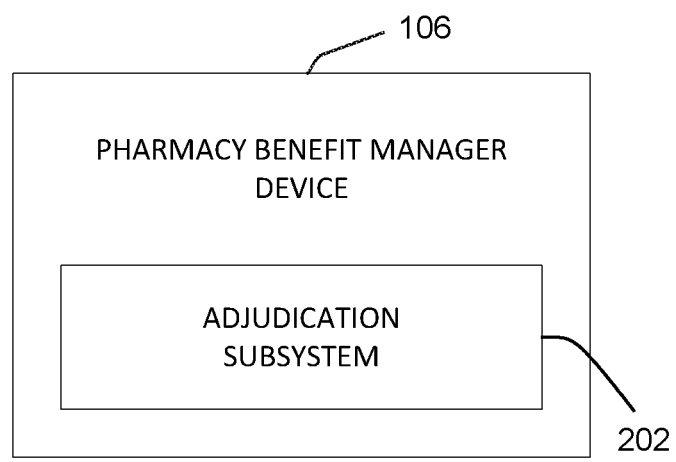
FIG. 3 is a block diagram of an example pharmacy benefit manager device that may be deployed within the system of FIG. 1, according to an example embodiment.

FIG. 3 illustrates the pharmacy benefit manager device 106, according to an example embodiment. The pharmacy benefit manager device 106 may be deployed in the system 100, or may otherwise be used.

The pharmacy benefit manager device 106 may include the adjudication subsystem 202. In some embodiments, the adjudication subsystem 202 may provide server-side functionality to the healthcare provider device 108. By way of example, the adjudication subsystem 202 may be deployed in both the healthcare provider device 108 and the pharmacy benefit manager device 106. The healthcare provider device 108 may then perform some of the functionality while other functionality is performed by the pharmacy benefit manager device 106.

Figure 4A:
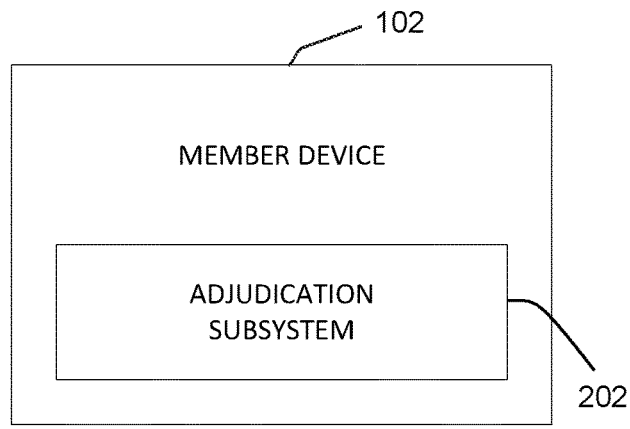
FIG. 4A is a block diagram of an example member device that may be deployed within the system of FIG. 1, according to an example embodiment.

FIG. 4A illustrates the member device 102, according to an example embodiment. The member device 102 may be deployed in the system 100, or may otherwise be used.

The member device 102 may include the adjudication subsystem 202. In some embodiments, the adjudication subsystem 202 may provide server-side functionality to the healthcare provider device 108 and/or the pharmacy benefit manager device 106. By way of example, the adjudication subsystem 202 may be deployed in the healthcare provider device 108, the pharmacy benefit manager device 106, and the member device 102.

Figure 4B:
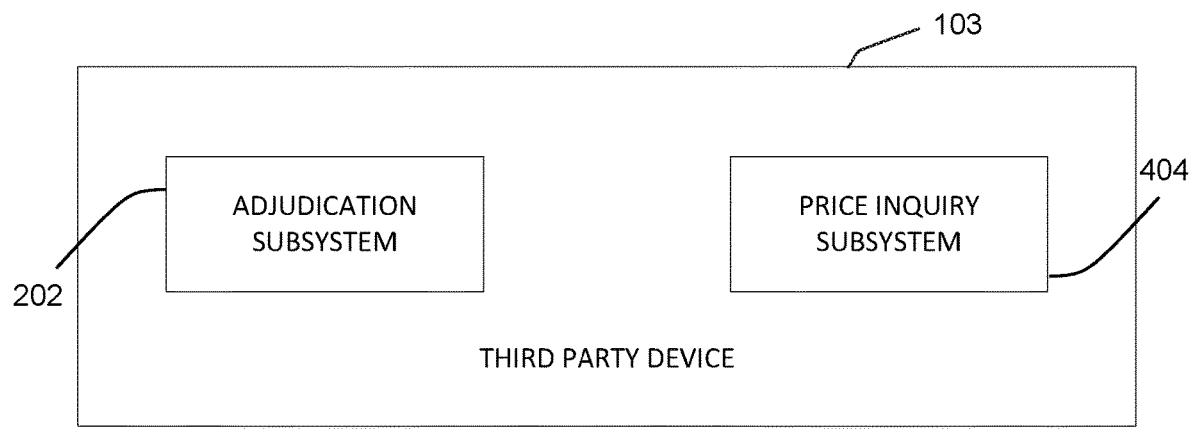
FIG. 4B is a block diagram of an example third party device that may be deployed within the system of FIG. 1, according to an example embodiment.

FIG. 4B illustrates the third party device 103, according to an example embodiment. The third party device 103 may be deployed in the system 100, or may otherwise be used.

The third party device 103 may include the adjudication subsystem 202. In some embodiments, the adjudication subsystem 202 may provide server-side functionality to the healthcare provider device 108 and/or the pharmacy benefit manager device 106. By way of example, the adjudication subsystem 202 may be deployed in the healthcare provider device 108, the pharmacy benefit manager device 106, and the third party device 103.

The third party device 103 also includes a price inquiry subsystem 404. The price inquiry subsystem 404 may provide an interface for receiving member data 112, claims data 114, or pharmacy data 116 from a person seeking drug pricing and co-pay information (i.e. adjudication results). The price inquiry subsystem 404 may further include subroutines that interface with APIs made available by the pharmacy benefit manager device 106, and the subroutines may include an indication that the adjudication request is merely a price inquiry and not for drug dispensing. This indicator (e.g. dispensing parameter) is used by the pharmacy benefit manager device 106 to stop the adjudication process before drugs are dispensed and pharmacies are reimbursed. This indicator may also identify the request as coming from a third party device 103 rather than a member device 102.

Figure 5:
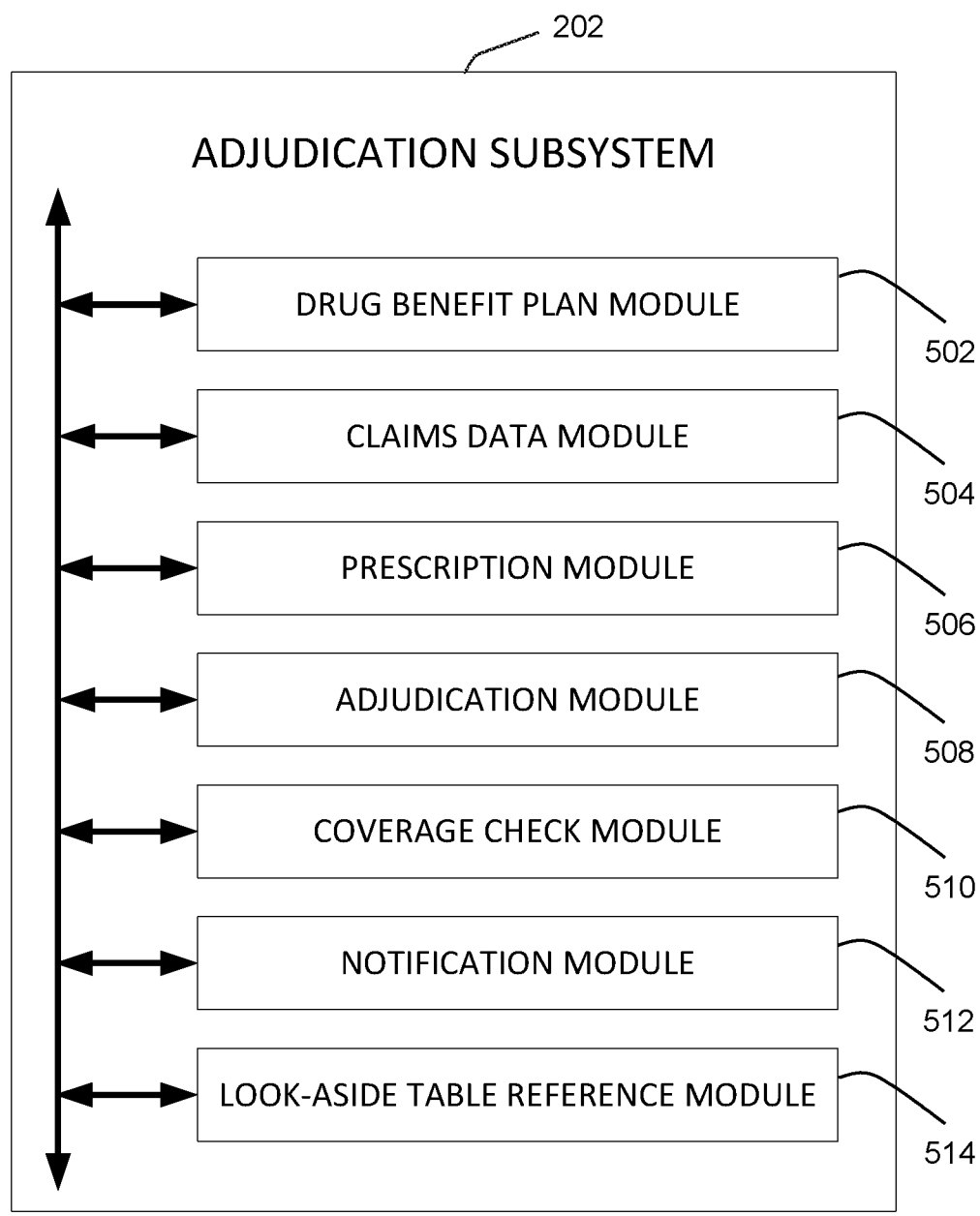
FIG. 5 is a block diagram of an example adjudication subsystem that may be deployed within the healthcare provider device of FIG. 2, the pharmacy benefit manager device of FIG. 3, the member device of FIG. 4A, or the third party device of FIG. 4B, according to an example embodiment.

FIG. 5 illustrates an example adjudication subsystem 202 that may be deployed in the member device 102, third party device 103, the pharmacy benefit manager device 106, the healthcare provider device 108, or otherwise deployed in another system. One or more modules are communicatively coupled and included in the adjudication subsystem 202 to enable claim adjudication. The modules of the adjudication subsystem 202 that may be included are the drug benefit plan module 502, the claims data module 504, the prescription module 506, the adjudication module 508, the notification module 510, and a look-aside table reference module 514. Other modules may also be included.

In some embodiments, the modules of the adjudication subsystem 202 may be distributed so that some of the modules are deployed in the member device 102, some of the modules are deployed in the third party device 103, some modules are deployed in the pharmacy benefit manager device 106, and some module are deployed in the healthcare provider device 108. In one embodiment, the modules are deployed in memory and executed by a processor coupled to the memory. The functionality contained within the modules 502-512 may be combined into a lesser number of modules, further divided among a greater number of modules, or redistributed among existing modules. Other configurations including the functionality of the modules 502-512 may be used.

The drug benefit plan module 502 may determine the status of a drug benefit plan of the member. The drug plan benefit module 502 may determine which drug benefit plan that is associated with the member.

A claims data module 504 may access claims data associated with the member. In some embodiments, the claims data module 504 may access the database 110 to access member data 112, claims data 114, or pharmacy data 116. In some embodiments, the claims data module 504 is able to access claims data associated with the member from one or more benefit plans and additional identifying information of the member to verify the identity of the member.

The claims data module 504 may receive the pharmacy data 116. The pharmacy data 116 for all pharmacies, all pharmacies in pharmacy network associations of the client, all pharmacies in a particular network association, all pharmacies in pharmacy network associations of the client within a particular geographic area or within a particular geographic range from a starting point, or otherwise may be received. The pharmacy data 116 may be received periodically by the claims data module 504 on the pharmacy benefit manager device 106.

A prescription module 506 may identify a prescription based on the claims data. In some embodiments, the prescription module 506 may use the claims data accessed by the claims data module 504 to identify a prescription of a member. In some embodiments, a prescription of a member is an existing prescription of a prescription drug for the member where the member has recently had the prescription filled.

An adjudication module 508 may perform at least one adjudication operation for the prescription prior to receiving a new request for the prescription or in response to a price inquiry. In some embodiments, the adjudication module 508 may perform one or more operations for the prescription or for the price inquiry. In some embodiments, the adjudication module 508 may determine the price of the prescription drug of the prescription for one or more pharmacies capable of fulfilling the prescription. In some embodiments, the adjudication module 508 may determine the co-pay amount for the prescription drug based on the drug benefit plan of the member. In some embodiments, the adjudication module 508 may determine the amount to reimburse the pharmacy filling the prescription based on the drug benefit plan of the member. In some embodiments, the adjudication module 508 may identify possible side effects of the prescription drug. In some embodiments, the adjudication module 508 may identify if the prescription drug conflicts with any other drugs taken by the member. The adjudication module 508 may identify possible alternative prescription drugs, such as those in the same therapy class, but different manufacturer or those in different therapy classes. The adjudication module 508 may save the price of the prescription drug, the co-pay amount, the side effects, and the possible alternative prescription drugs in the database 110 as an adjudication record after performing adjudication. The adjudication record may also include the member data 112, the claims data 114, and the pharmacy data 116 the generated the price of the prescription drug, the co-pay amount, the side effects, and the possible alternative prescription drugs through adjudication. The adjudication module 508 may execute an adjudication task prior to receipt of a prescription being received for adjudication or prior to a new price inquiry. A single adjudication task or multiple adjudication tasks may be executed.

A notification module 510 may generate a notification to the member based on the adjudication. In some embodiments, the notification module 510 may generate an email, text message, voice message, letter, or other type of communication. The notification may be a summary of the adjudication and may at least include a drug price and a co-pay amount. In some embodiments, the notification may contain a detailed description regarding the factors that may have influenced the drug pricing. In some embodiments, the notification may be a message to the pharmacy benefit manager to speak with a care coordinator. The care coordinator may provide details to the member regarding the price determination.

The look-aside table reference module 512 receives member data 112, the claims data 114, and the pharmacy data 116 from the member device 102 or the third party device 103. The look-aside table reference module 512 may also reference a current time when the look-aside table reference module 512 received the member data 112, the claims data 114, and the pharmacy data 116. The look-aside table reference module 512 may access and query the look-aside table 118 in the database 110 to determine if any adjudication records have member data 112, claims data 114, and pharmacy data 116 that matches, significantly matches, or corresponds to the received member data 112, claims data 114, and pharmacy data 116. The look-aside table reference module 512 accesses and provides information stored in a corresponding adjudication record if a similar record is found in the database 110. The look-aside table reference module 512 may also compare the current time with a time stamp stored by the adjudication record to determine if the adjudication record in the look-aside table 118 has data generated within a predetermined time period (e.g. within 24-48 hours of the current time).

Figure 6:
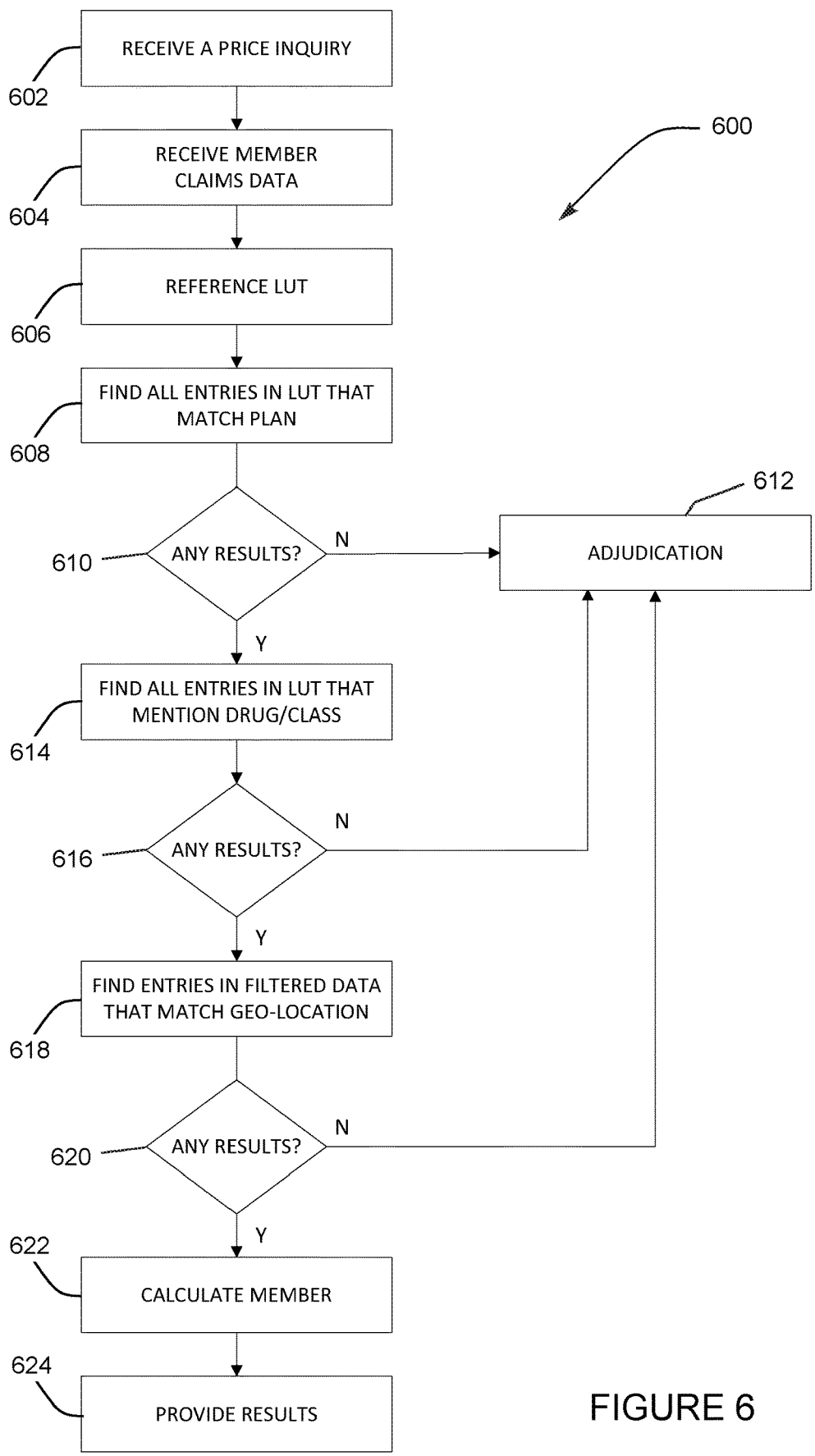
FIG. 6 is a block diagram of a flowchart illustrating methods for referencing a look-aside table, according to an example embodiment.

FIG. 6 illustrates a method 600 for claim adjudication using the look-aside table 118, according to an example embodiment. The method 600 may be performed by the pharmacy benefit manager device 106, partially by the pharmacy benefit manager device 106 and partially by the member device 102, the third party device 103, and/or the healthcare provider device 108, or may be otherwise performed. For the sake of simplicity, the pharmacy benefit manager device 106 will be described as performing the steps of the method 600, but the embodiments described herein are not so limited.

The pharmacy benefit manager device 106 may receive a price inquiry, data request, or data from a user or a data source in step 602. The request received in step 602 may also be a request to dispense a drug from the member device 102. The price inquiry may come from either the member device 102 or the third party device 103. As part of the received price inquiry, the pharmacy benefit manager device 106 may receive a member identifier, a drug identifier, and a geolocation identifier (or other data). In some embodiments, the price inquiry may also request pricing from a single pharmacy or multiple pharmacies within a specific geographic range of the received geolocation identifier. The request received at step 602 may include a parameter indicating that the request is a price inquiry or that the request is for dispensing of drugs. In some embodiments, if the parameter indicates that the request is for the dispensing of drugs, the method 600 may immediately jump to step 612 where the adjudication function is performed.

The pharmacy benefit manager device 106 may use the member identifier to reference and receive the member data 112 in the database 110 in step 604, for example using the drug benefit plan module 502, the claims data module 504, and the prescription module 506. The member identifier may also be used to reference and receive claims data 114 in the database. The member data 112 and the claims data 114 may be used in the adjudication function. In some embodiments, claims data 112 may include data indicating eligibility for a prescription drug, access to the prescription drug, access to supporting information associated with the prescription drug, data associated with a provider of the prescription drug, demographic information associated with the member, data associated with a pharmacy dispensing the prescription drug, data indicating whether prior authorization is required before dispensing the prescribed drug in ensure the drug is being used for a medically-approved indication, or any combination thereof. In some embodiments, only member data 112 is referenced in step 604 to find or determine a drug benefit plan associated with the member identifier (or other identifier based on received data). From the received member data 112, the pharmacy benefit manager device 106 may determine a drug benefit plan associated with the member, which may be represented by a drug benefit plan identifier.

The pharmacy benefit manager device 106 may access the look-aside table 118 in step 606 using the look-aside table reference module 514. In some embodiments, accessing the look-aside table 118 may include accessing the database 110. In other embodiments, the look-aside table 118 may be locally saved on the pharmacy benefit manager device 106. In some embodiments, only the active look-aside table is referenced and accessed, but the historical look-aside table 118 or all entries in the look-aside table 118 may be accessed in step 606. In some embodiments, the look-aside table 118 may include a plurality of field parameters, such as the drug benefit plan identifier.

The pharmacy benefit manager device 106 may filter the data in the look-aside table 118 after selecting a field value associated with one of the field parameters associated with the member identifier. Filtering may occur by finding all data in the look-aside table 118 that matches or corresponds to the determined drug benefit plan in step 608. The pharmacy benefit manager device 106 may use the drug benefit plan identifier to find all data entries in the look-aside table 118 that match the determined drug benefit plan of the requesting member. The data matching or corresponding to the determined drug benefit plan of the requesting member may be called a first filtered data subset. All data not matching or not corresponding to the drug benefit plan identifier is ignored in subsequent processing steps of the method 600.

The pharmacy benefit manager device 106 may determine if any entries in the look-aside table 118 match or correspond to the drug benefit plan identifier in step 610. If no results are found in the look-aside table 118, the pharmacy benefit manager device 106 performs the adjudication function using the adjudication module 508 in step 612.

In some embodiments, the adjudication operation 612 may include determining the price of the prescription drug for one or more pharmacies capable of fulfilling the prescription. In some embodiments, prices for the prescription drug may be determined only for pharmacies that are within an identified pharmacy network. In some embodiments, prices for the prescription drug may be determined for pharmacies within an identified geographic area. In some embodiments, prices for the prescription drug may be determined for pharmacies identified using other criteria.

In some embodiments, the adjudication operation 612 may include identifying possible side effects of the prescription drug. The adjudication operation 612 may include identifying possible alternative prescription drugs, such as those in the same therapy class, but different manufacturer (e.g., identifying generic drugs when prescribed a brand drug and vice versa). The adjudication operation 612 may include identifying possible alternative prescription drugs, such as those in different therapy classes. The adjudication subsystem 202 may also identify possible side effects of the alternative prescription drugs as well as any indication of possible side effects resulting from a mixture of the prescription drug and other prescription and/or non-prescription drugs taken by the member. In some embodiments, identifying the other prescription and/or non-prescription drugs taken by the member may be another adjudication operation 612 of the adjudication subsystem 202. In some embodiments, the price of the prescribed drug at each of the pharmacies capable of fulfilling the prescription may be transmitted to the member.

In some embodiments, the adjudication operation 612 may include ranking or rating the one or more pharmacies capable of filling the prescription of the member. In some embodiments, the ranking or rating generated by the adjudication subsystem may be based on pharmacy data, pricing data, member feedback, or other criteria. The ranking and/or rating generated by the adjudication subsystem 202 may be sortable or otherwise manipulated by the member to identify a pharmacy that may meet the specific needs of the member based on the criteria provided by the member.

Finally, the adjudication operation 612 may save adjudication results in the form of adjudication records to the look-aside table 118. The adjudication records may comprises, among other things, drug identifier, drug price, drug classification, pharmacy identifier, drug benefit plan identifier, pharmacy locality identifier (e.g. zip code), and a time stamp when the adjudication operation was completed. Indeed, anytime the pharmacy benefit manager device 106 completes the adjudication function 612, whether in response to filling a drug dispensing request or responding to a price inquiry, the pharmacy benefit manager device 106 populates data to the look-aside table 118.

If, as a result of the filtering step in step 608, any entries matching or corresponding to the drug benefit plan identifier are found, the pharmacy benefit manager device 106 may filter the first filtered data subset of the look-aside table 118 by finding entries of the first filtered data subset that match or correspond to the identified drug or drug classification in step 614. The pharmacy benefit manager device 106 may use the drug identifier to find all data entries in the look-aside table 118 that match or correspond to the determined drug or drug classification of the requesting member and match or correspond to the determined drug benefit plan of the requesting member. The data matching or corresponding to the determined drug benefit plan and the drug identifier may be called a second filtered data subset. All data not matching or not corresponding to the drug benefit plan identifier and the drug identifier is ignored in subsequent processing steps of the method 600.

The pharmacy benefit manager device 106 may determine if any entries in the first filtered data subset match or correspond to the drug identifier in step 616. If no results are found, the pharmacy benefit manager device 106 performs adjudication using the received member data, claims data, and pharmacy data in step 612.

If, as a result of the filtering step in step 614, any entries in the look-aside table 118 matching or corresponding to the drug benefit plan identifier and the drug identifier are found, the pharmacy benefit manager device 106 may further filter the second filtered data subset of the look-aside table 118 by finding all entries of the second filtered data subset that also matches or corresponds to the geolocation identifier in step 618. The pharmacy benefit manager device 106 may use the geolocation identifier to find all data entries of the second filtered data subset that also match or correspond to the submitted geolocation of the requesting member. All filtered data (i.e. data not matching or corresponding to the drug benefit plan identifier, the drug identifier, and the geolocation identifier) is ignored in subsequent processing steps of the method 600.

Data may be determined to match or correspond to the geolocation identifier according to a number of methods. For example, the geolocation identifier may be a specific pharmacy (e.g. the Walgreens on Belmont Avenue in Chicago, Ill.). In this example, the geolocation identifier may match or correspond to data in the look-aside table 118 when the look-aside table 118 has an adjudication result stored for that specific pharmacy. In another example, the geolocation may be a zip code. In this example, the geolocation identifier may match or correspond to data in the look-aside table 118 when the look-aside table 118 has an adjudication result stored for any participating or eligible pharmacy in the submitted zip code. The pharmacy benefit manager device 106 may also identify adjacent zip codes using the received zip code. The pharmacy benefit manager device 106 may include a table that stores adjacent zip codes for every zip code in the country. In another example, the geolocation may be a city and state. In this example, the geolocation identifier may match or correspond to data in the look-aside table 118 when the look-aside table 118 has an adjudication result stored for any participating or eligible pharmacy in the submitted city and state. In yet another example, the geolocation may be GPS coordinates. In this example, the geolocation identifier may match or correspond to data in the look-aside table 118 when the look-aside table has an adjudication result stored for a pharmacy within a given distance of the GPS coordinates. A searchable distance may be a parameter set by the user (e.g. "show me pricing data for all pharmacies within 5 miles of me") when submitting the price inquiry or the searchable distance parameter may be set automatically. The GPS coordinates may be used to determine a zip code, a city and state, a neighborhood, a locality, or any other geolocator. In some embodiments, the look-aside table 118 or the pharmacy data 116 may store a GPS coordinate of each pharmacy and determine all pharmacies within the searchable distance parameter by comparing the member's GPS coordinates to the pharmacy coordinates. The pharmacy benefit manager device 106 may determine a member's GPS coordinates by requesting the member device 102 to determine GPS coordinates and provide the determined GPS coordinates using a GPS device included within the member device 102.

The pharmacy benefit manager device 106 may determine if an entry in the second filtered data subset matches or corresponds to the geolocation identifier in step 620. If no results are found, the pharmacy benefit manager device 106 performs the adjudication function using the received member data, claims data, and pharmacy data in step 612.

As a result of the filtering performed by steps 608, 614, and 618, if at least one entry is found, then the drug price is transmitted using that at least one entry. The drug price may be transmitted by the notification module 510. The pharmacy benefit manager device 106 may calculate a member contribution based on the drug benefit plan rules and the drug price stored in the look-aside table 118 in step 622. In step 624, the member contribution (e.g. co-pay) and the drug price are provided.

In some embodiments, the method 600 may reference a time stamp associated with the determined entry matching or corresponding to the drug benefit plan identifier, the drug identifier, and the geolocation identifier to make sure that the entry is within a time period. This step may occur if the look-aside table 118 includes historical data or if the look-aside table reference module 512 does not only reference an active look-aside table. This step may include determining if the time stamp is within a time period (e.g. within the last 24-48 hours). The time period may be a user-selected parameter provided at step 602, and the user can set the time period to be any value (e.g. 72 hours, 100 hours, 2 weeks, 1 month).

The method 600 is not limited to the order of the filter steps 608, 614, 616 described in regard to FIG. 6. Indeed, the first filtering step may be based on locality, followed by filtering based on drug benefit plan, and then followed by filtering based on drug identification. In another embodiment, the first filtering step may be based on drug identification, the second filtering step may be based on plan identification, and the third filtering step may be based on locality. Additional filtering steps are also contemplated, such as filtering based on pharmacy chain (e.g. Walgreens or CVS), filtering based on drug classification (e.g. to find a drug and all drug equivalents), filtering based on timestamp, or any other filtering method using the data categories stored in the look-aside table 118.

The filtering method and use of the look-aside table 118 results in significant processor bandwidth savings. Compared to the amount of processing necessary to perform all the adjudication functions of step 612, the filtering steps 608, 614, 616 use significantly less processing time and processing bandwidth because a processor is merely iterating through a database table rather than processing numerous variables to perform full adjudication (e.g. checking for side effects, determining pharmacy networks, etc.). The method 600 also provides drug prices and member contributions (e.g. co-pays) much faster than if the full adjudication function 612 were to be performed. Therefore, price inquiries are provided much faster and the processor can calculate more price inquires. This bandwidth savings means that a single processor can perform the functions of a mainframe. As mentioned above, performing a full adjudication for a price request requires sharing a great deal of information between the devices 102, 103, 106, 108 and also processing those numerous variables according to multiple considerations (e.g. is the drug incompatible with another prescription drug being taken by the client, tax considerations for a locality, drug laws specific to a locality). By removing this step for redundant price inquiries, the system hardware is able to respond to price inquires and provide price quotes much faster without an improvement to the computer hardware itself.

In some embodiments, the system 100 may determine computing resources of the system 100, such as bandwidth, processor load, number of requests, number of prescription requests requiring adjudication, or any other computer metric that measures load on the computer system 100. The system 100 may reference the look-up table when the measured load is higher than a threshold. For example, if the amount of adjudication requests is relatively low, the system may perform full adjudication in response to a price inquiry if the computer load is lower than the threshold. The system 100 may calculate computing load by finding a direct relationship between the number of requests and the computer load.

Figure 7:
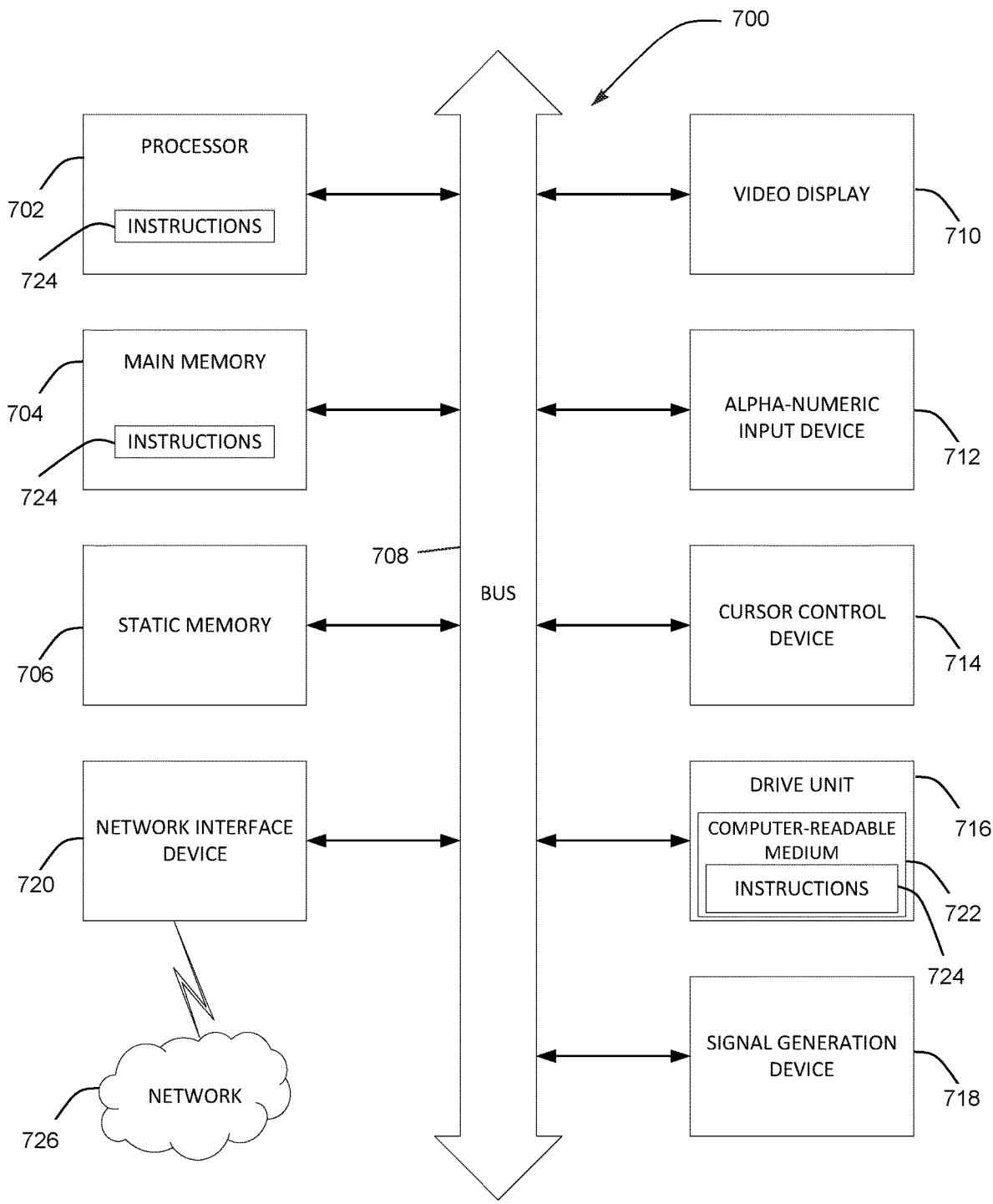
FIG. 7 is a block diagram of a machine in the example form of a computer system within which a set of instructions for causing the machine to perform any one or more of the methodologies discussed herein may be executed or stored.

FIG. 7 shows a block diagram of a machine in the example form of a computer system 700 within which a set of instructions may be executed causing the machine to perform any one or more of the methods, processes, operations, or methodologies discussed herein. The member device 102, the third party device 103, the pharmacy benefit manager device 106, and/or the healthcare provide device 108 may include the functionality of the one or more computer systems 700.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702 (e.g., a central processing unit (CPU) a graphics processing unit (GPU) or both), a main memory 704 and a static memory 706, which communicate with each other via a bus 708. The processor 712 may include a single discrete electronic processing element or a multiple electronic processing elements that can execute the processes, flows, and methods described herein.

The computer system 700 further includes a video display unit 710 (e.g., a liquid crystal display (LCD) or a cathode ray tube (CRT)). The computer system 700 also includes an alphanumeric input device 712 (e.g., a keyboard), a cursor control device 714 (e.g., a mouse), a drive unit 716, a signal generation device 718 (e.g., a speaker) and a network interface device 720.

The drive unit 716 includes a computer-readable medium 722 on which is stored one or more sets of instructions (e.g., software 724) embodying any one or more of the methodologies or functions described herein. The software 724 may also reside, completely or at least partially, within the main memory 704 and/or within the processor 712 during execution thereof by the computer system 700, the main memory 704 and the processor 712, also constituting computer-readable media.

The software 724 may further be transmitted or received over a network 726 via the network interface device 720.

While the computer-readable medium 722 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a first identifier associated with a user can be determined, and a second identifier associated with the user can be received. A table storing a plurality of adjudication results may be accessed, where each adjudication result of the plurality of adjudication results is associated with at least one variable. The plurality of adjudication results in the table can be filtered by determining which adjudication results of the plurality of adjudication results are associated with a variable matching or corresponding to the first identifier, where filtering a first time creates a first subset of adjudication results when at least one adjudication result is associated with the first identifier. The first subset of adjudication results can be provided when the processor determines that at least one adjudication result of the plurality of adjudication results is associated with the first identifier, and an adjudication function can be performed when none of the plurality of adjudication results are associated the first identifier.

In an example embodiment, a system may include a processor and a memory coupled to the processor. A drug benefit plan module may be deployed in the memory and executed by the processor to determine a first identifier associated with a user and receive a second identifier associated with the user. A look-aside table reference module may be deployed in the memory and executed by the processor to (1) access a table storing a plurality of adjudication results, where each adjudication result of the plurality of adjudication results is associated with at least one variable, and (2) filter the plurality of adjudication results in the table by determining which adjudication result(s) of the plurality of adjudication results are associated with a variable matching or corresponding to the first identifier, where filtering a first time creates a first subset of adjudication results when at least one adjudication result is associated with the first identifier. A notification module may be deployed in the memory and executed by the processor to provide the first subset of adjudication results when the processor determines that at least one adjudication result of the plurality of adjudication results is associated with the first identifier. An adjudication module may be deployed in the memory and executed by the processor to perform an adjudication function when none of the plurality of adjudication results are associated the first identifier.

Thus, methods and systems for referencing a look-aside table have been described. Although embodiments of the present disclosure have been described with reference to specific example embodiments, it will be evident that various modifications and changes may be made to these embodiments without departing from the broader spirit and scope of the embodiments of the present disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A system comprising:
   a processor and a memory coupled to the processor;
   a drug benefit plan module deployed in the memory and executed by the processor to (a) receive data from a data source, (b) receive a data processing request indicating a request to perform a first function, and (c) determine a first identifier, a second identifier, and a third identifier associated with the data source based on the received data;
   a look-aside table reference module deployed in the memory and executed by the processor to:
   access a data computation table storing a plurality of adjudication results including a plurality of field parameters,
   filter the plurality of adjudication results in the data computation table by determining whether at least one of the plurality of adjudication results includes one of the plurality of field parameters that matches or corresponds to the first identifier and creating a first subset of filtered adjudication results from the plurality of adjudication results when the plurality of adjudication results includes one of the plurality of field parameters that matches or corresponds to the first identifier;
   when the plurality of adjudication results includes one of the plurality of field parameters that matches or corresponds to the first identifier, filter the first subset of filtered adjudication results in the data computation table by determining whether at least one of the first subset of filtered adjudication results includes one of the plurality of field parameters that matches or corresponds to the second identifier and creating a second subset of filtered adjudication results when the first subset of filtered adjudication results includes one of the plurality of field parameters that matches or corresponds to the second identifier;
   when the first subset of filtered adjudication results includes one of the plurality of field parameters that matches or corresponds to the second identifier, filter the second subset of filtered adjudication results in the data computation table by determining whether at least one of the second subset of filtered adjudication results includes one of the plurality of field parameters that matches or corresponds to the third identifier and creating a third subset of filtered adjudication results when the second subset of filtered adjudication results includes one of the plurality of field parameters that matches or corresponds to the third identifier;
   a notification module deployed in the memory and executed by the processor to transmit the third subset of adjudication results; and
   an adjudication module deployed in the memory and executed by the processor to perform an adjudication function in response to determining that the plurality of adjudication results fails to include one of the plurality of field parameters that matches or corresponds to the first identifier, the first subset of filtered adjudication results fails to include one of the plurality of field parameters that matches or corresponds to the second identifier, or the second subset of filtered adjudication results fails to include one of the plurality of field parameters that matches or corresponds to the third identifier,
   wherein the first identifier indicates a drug benefit plan associated with the data source,
   wherein the second identifier indicates a drug classification,
   wherein the third identifier indicates a geographic indicator, and
   wherein the notification module further lists one or more pharmacies capable of fulfilling a prescription drug corresponding to the drug classification in a geographical region associated with the geographic indicator when transmitting the third subset of adjudication results.

2. A method comprising:
   receiving, by processor, data from a data source;
   receiving, by the processor, a data processing request indicating a request to perform a first function;
   determining, by the processor, a first identifier, a second identifier, and a third identifier associated with the data source based on the received data;
   accessing, by the processor, a data computation table storing a plurality of adjudication results including a plurality of field parameters,
   filtering, by the processor, the plurality of adjudication results in the data computation table by determining whether at least one of the plurality of adjudication results includes one of the plurality of field parameters that matches or corresponds to the first identifier and creating a first subset of filtered adjudication results from the plurality of adjudication results when the plurality of adjudication results includes one of the plurality of field parameters that matches or corresponds to the first identifier;
   when the plurality of adjudication results includes one of the plurality of field parameters that matches or corresponds to the first identifier, filtering, by the processor, the first subset of filtered adjudication results in the data computation table by determining whether at least one of the first subset of filtered adjudication results includes one of the plurality of field parameters that matches or corresponds to the second identifier and creating a second subset of filtered adjudication results when the first subset of filtered adjudication results includes one of the plurality of field parameters that matches or corresponds to the second identifier;
   when the first subset of filtered adjudication results includes one of the plurality of field parameters that matches or corresponds to the second identifier, filtering, by the processor, the second subset of filtered adjudication results in the data computation table by determining whether at least one of the second subset of filtered adjudication results includes one of the plurality of field parameters that matches or corresponds to the third identifier and creating a third subset of filtered adjudication results when the second subset of filtered adjudication results includes one of the plurality of field parameters that matches or corresponds to the third identifier;
   transmitting, by the processor, the third subset of adjudication results; and
   in response to a determination that the plurality of adjudication results fails to include one of the plurality of field parameters that matches or corresponds to the first identifier, the first subset of filtered adjudication results fails to include one of the plurality of field parameters that matches or corresponds to the second identifier, or the second subset of filtered adjudication results fails to include one of the plurality of field parameters that matches or corresponds to the third identifier performing, by the processor, an adjudication function that calculates a drug price based on the received data, wherein the first identifier indicates a drug benefit plan associated with a patient associated with the data source, wherein the second identifier indicates a drug classification, wherein the third identifier indicates a geographic indicator, and wherein the transmitting step further comprises listing one or more pharmacies capable of fulfilling a prescription drug corresponding to the drug classification in a geographical region associated with the geographic indicator.

3. The method of claim 2, further comprising determining the drug benefit plan based on a member identifier received from the data source.

4. The method of claim 2, wherein performing the adjudication function comprises calculating, by the processor, a drug price based on the received data when none of the plurality of adjudication results is associated with the first identifier and the second identifier.

5. The method of claim 2, wherein the geographic indicator is a zip code, and wherein the transmitting step further comprises listing all pharmacies capable of filling the prescription drug in the zip code.

6. The method of claim 5, further comprising:
determining, by the processor, adjacent zip codes to the zip code indicated by the geographic identifier, wherein the transmitting step further comprises listing all pharmacies capable of filling the prescription drug in the zip code and the adjacent zip codes.

7. The method of claim 2, further comprising:
receiving, by the processor, global positioning system (GPS) coordinates from a user device associated with the data source; and
determining, by the processor, a zip code associated with the GPS coordinates and using the zip code as the geographic indicator.

8. The method of claim 2, further comprising: determining, by the processor, a current time;
accessing, by the processor, a time stamp associated with each adjudication result in the third subset of adjudication results, the time stamp being a recordation of time associated with adjudication; and
determining, by the processor, whether each time stamp associated with each adjudication result in the third subset of adjudication results is within a time period of the current time,
wherein the transmitting step further comprises transmitting only the third subset of adjudication results that have time stamps within the time period of the current time.

9. The method of claim 8, wherein the processor receives the time period from a user device associated with the data source.

10. The method of claim 2, further comprising: determining, by the processor, a current time;
accessing, by the processor, a time stamp associated with each adjudication result in the plurality of adjudication results, the time stamp being a recordation of time associated with adjudication; and
moving, by the processor, an adjudication result of the plurality of adjudication results having a time stamp that is not within a time period of the current time from an active data computation table to a historical data computation table,
wherein the accessing the data computation table step further comprises accessing only the active data computation table.

11. The method of claim 2, wherein each adjudication result of the plurality of adjudication results comprises a drug price for the prescription drug calculated based on at least a drug benefit plan.

12. The method of claim 11, further comprising:
calculating, by the processor, a member contribution to the drug price based on a provision of the drug benefit plan specific to the patient associated with the data source.

13. The method of claim 2, further comprising:
storing, by the processor, a new adjudication result in the data computation table after performing the adjudication function.

14. The method of claim 2, wherein the adjudication function comprises determining a price of the prescription drug for the one or more pharmacies capable of fulfilling the prescription drug, determining a co-pay amount for the prescription drug based on the drug benefit plan of the patient associated with the data source, determining an amount to reimburse a pharmacy filling the prescription drug based on the drug benefit plan of the patient associated with the data source, identifying possible side effects of the prescription drug, identifying if the prescription drug conflicts with any other drugs taken by a patient associated with the data source, identifying possible alternative prescription drugs in a same therapy class as the prescription drug, or identifying a different manufacturer of the prescription drug.

15. The method of claim 2, wherein the first identifier is received through an application programming interface.

16. The method of claim 2, wherein the first function is a drug price inquiry.

17. A non-transitory machine-readable medium comprising instructions,
which when executed by one or more processors, cause the one or more processors to perform the following operations:
receive data from a data source;
receive a data processing request indicating a request to perform a first function;
determine a first identifier, a second identifier, and a third identifier associated with the data source based on the received data;
access a data computation table storing a plurality of adjudication results including a plurality of field parameters;
filter the plurality of adjudication results in the data computation table by determining whether at least one of the plurality of adjudication results includes one of the plurality of field parameters that matches or corresponds to the first identifier and creating a first subset of filtered adjudication results from the plurality of adjudication results when the plurality of adjudication results includes one of the plurality of field parameters that matches or corresponds to the first identifier;
when the plurality of adjudication results includes one of the plurality of field parameters that matches or corresponds to the first identifier, filter the first subset of filtered adjudication results in the data computation table by determining whether at least one of the first subset of filtered adjudication results includes one of the plurality of field parameters that matches or corresponds to the second identifier and creating a second subset of filtered adjudication results when the first subset of filtered adjudication results includes one of the plurality of field parameters that matches or corresponds to the second identifier;

when the first subset of filtered adjudication results includes one of the plurality of field parameters that matches or corresponds to the second identifier, filter the second subset of filtered adjudication results in the data computation table by determining whether at least one of the second subset of filtered adjudication results includes one of the plurality of field parameters that matches or corresponds to the third identifier and creating a third subset of filtered adjudication results when the second subset of filtered adjudication results includes one of the plurality of field parameters that matches or corresponds to the third identifier;

transmit the third subset of adjudication results; and in response to a determination that the plurality of adjudication results fails to include one of the plurality of field parameters that matches or corresponds to the first identifier, the first subset of filtered adjudication results fails to include one of the plurality of field parameters that matches or corresponds to the second identifier, or the second subset of filtered adjudication results fails to include one of the plurality of field parameters that matches or corresponds to the third identifier perform an adjudication function that calculates a drug price based on the received data, wherein the first identifier indicates a drug benefit plan associated with the data source wherein the second identifier indicates a drug classification, and wherein the third identifier indicates a geographic indicator, and wherein the one or more processors list one or more pharmacies capable of filling a prescription drug corresponding to the drug classification in a geographical region associated with the geographic indicator when transmitting the third subset of adjudication results.

* * * * *